US007066180B2

(12) United States Patent
Aylsworth et al.

(10) Patent No.: US 7,066,180 B2
(45) Date of Patent: Jun. 27, 2006

(54) METHOD AND SYSTEM FOR MEASURING AIRFLOW OF NARES

(75) Inventors: Alonzo C. Aylsworth, Wildwood, MO (US); Lawrence C. Spector, Austin, TX (US)

(73) Assignee: Airmatrix Technologies, Inc., Wildwood, MO (US)

( * ) Notice: Subject to any disclaimer, the term of this patent is extended or adjusted under 35 U.S.C. 154(b) by 390 days.

(21) Appl. No.: 10/616,042

(22) Filed: Jul. 9, 2003

(65) Prior Publication Data

US 2005/0005942 A1   Jan. 13, 2005

(51) Int. Cl.
*A61M 15/08*   (2006.01)
(52) U.S. Cl. .............................. 128/207.18; 128/204.23
(58) Field of Classification Search ........... 128/203.22, 128/204.23, 204.26, 206.11, 207.18; 600/532, 600/535, 537, 538
See application file for complete search history.

(56) References Cited

U.S. PATENT DOCUMENTS

| 2,007,287 | A | * | 7/1935 | Shotton ................. 128/203.22 |
| 2,208,633 | A | * | 7/1940 | Heidbrink .............. 128/203.28 |
| 3,566,862 | A | * | 3/1971 | Schuh et al. ................. 601/44 |
| 4,054,133 | A | * | 10/1977 | Myers ................... 128/204.26 |
| 4,278,110 | A | * | 7/1981 | Price et al. ................. 137/805 |
| 4,428,372 | A | | 1/1984 | Beysel et al. |
| 4,457,303 | A | * | 7/1984 | Durkan ................. 128/204.24 |
| 4,519,399 | A | * | 5/1985 | Hori ........................... 600/537 |
| 4,602,644 | A | * | 7/1986 | DiBenedetto et al. ....... 600/538 |
| 4,706,664 | A | | 11/1987 | Snook et al. |
| 4,777,963 | A | * | 10/1988 | McKenna ................... 600/537 |
| 4,832,014 | A | * | 5/1989 | Perkins .................. 128/203.12 |
| 4,958,075 | A | * | 9/1990 | Mace et al. ................. 250/343 |
| 4,989,599 | A | * | 2/1991 | Carter ................... 128/207.18 |
| 5,005,571 | A | * | 4/1991 | Dietz .................... 128/205.25 |
| 5,046,491 | A | * | 9/1991 | Derrick ................. 128/200.24 |
| 5,069,222 | A | * | 12/1991 | McDonald, Jr. ............ 600/537 |
| 5,099,836 | A | * | 3/1992 | Rowland et al. ........ 128/204.23 |
| 5,134,995 | A | * | 8/1992 | Gruenke et al. ........ 128/204.23 |
| 5,137,017 | A | * | 8/1992 | Salter .................... 128/207.18 |
| 5,190,048 | A | * | 3/1993 | Wilkinson .................. 600/537 |
| 5,251,636 | A | * | 10/1993 | Neuman .................... 600/537 |
| 5,279,304 | A | * | 1/1994 | Einhorn et al. ............. 600/537 |
| 5,311,875 | A | * | 5/1994 | Stasz ......................... 600/537 |
| 5,335,656 | A | * | 8/1994 | Bowe et al. ........... 128/207.18 |
| 5,413,111 | A | * | 5/1995 | Wilkinson .................. 600/537 |
| 5,513,631 | A | * | 5/1996 | McWilliams ........... 128/204.23 |

(Continued)

OTHER PUBLICATIONS

Medline Industries, Inc. Products Brochure, "SleepStrip®, Disposable Sleep Apnea Screener,".

(Continued)

*Primary Examiner*—Aaron J. Lewis
(74) *Attorney, Agent, or Firm*—Mark E. Scott; Conley Rose, P.C.

(57) ABSTRACT

A method and system for measuring airflow through nares. One exemplary embodiment comprises: measuring an attribute of an airflow through a first naris; measuring an attribute of an airflow through a second naris; wherein measuring the attribute of the airflow through the first naris is accomplished without blocking the second naris; and wherein measuring the attribute of the airflow through the second naris is accomplished without blocking the first naris.

46 Claims, 4 Drawing Sheets

U.S. PATENT DOCUMENTS

| | | | |
|---|---|---|---|
| 5,704,345 A | | 1/1998 | Berthon-Jones |
| 5,755,224 A | | 5/1998 | Good et al. |
| 5,803,066 A | * | 9/1998 | Rapoport et al. ...... 128/204.23 |
| 5,839,434 A | | 11/1998 | Enterline |
| 5,890,490 A | | 4/1999 | Aylsworth et al. |
| 6,029,664 A | | 2/2000 | Zdrojkowski et al. |
| 6,152,134 A | | 11/2000 | Webber et al. |
| 6,155,986 A | * | 12/2000 | Brydon et al. .............. 600/538 |
| 6,183,423 B1 | | 2/2001 | Gaumond et al. |
| 6,213,955 B1 | * | 4/2001 | Karakasoglu et al. ....... 600/529 |
| 6,342,040 B1 | | 1/2002 | Starr et al. |
| 6,379,312 B1 | * | 4/2002 | O'Toole .................... 600/529 |
| 6,386,235 B1 | | 5/2002 | McCulloh et al. |
| 6,393,802 B1 | | 5/2002 | Bowser et al. |
| 6,394,088 B1 | | 5/2002 | Frye et al. |
| 6,398,739 B1 | | 6/2002 | Sullivan et al. |
| 6,446,630 B1 | | 9/2002 | Todd, Jr. |
| 6,565,517 B1 | * | 5/2003 | Rasmussen ................. 600/529 |
| 6,655,385 B1 | * | 12/2003 | Curti et al. ............ 128/207.18 |
| 6,805,126 B1 | * | 10/2004 | Dutkiewicz ........... 128/207.18 |
| 6,938,619 B1 | * | 9/2005 | Hickle .................. 128/207.18 |
| 2002/0029004 A1 | | 3/2002 | Starr et al. |

OTHER PUBLICATIONS

S.L.P. Ltd. Information Sheet, "SleepStrip® FAQ," SLP Ltd., 18 Hazfira Street, Tel-Aviv 67779, Israel.

T. Shochat et al., "The SleepStrip™: an apnoea screener for the early detection of sleep apnoea syndrome," European Respiratory Journal 2002, ISSN 0903-1936, vol. 19, pp. 121-126.

Salter Labs New Products Brochure, "New Product O$_2$XPRESS® Oxygen Conserver Device,".

Salter Labs Products Brochure, "ETCO$_2$ Sampling Cannulas,".

Hudson RCI Products Brochure, "Product Catalog, Cannulas, Masks, Tubing: Nasal Cannulas,".

RHINOMANOMETER [online], Retrieved from the Internet: <URL: http://www.nagelnetwork.com/rhino.htm.

U.S. Appl. No. 10/287,800, filed Nov. 5, 2002, for "Therapeutic Gas Conserver and Control," Alonzo C. Aylsworth and Gregory R. Miller.

* cited by examiner

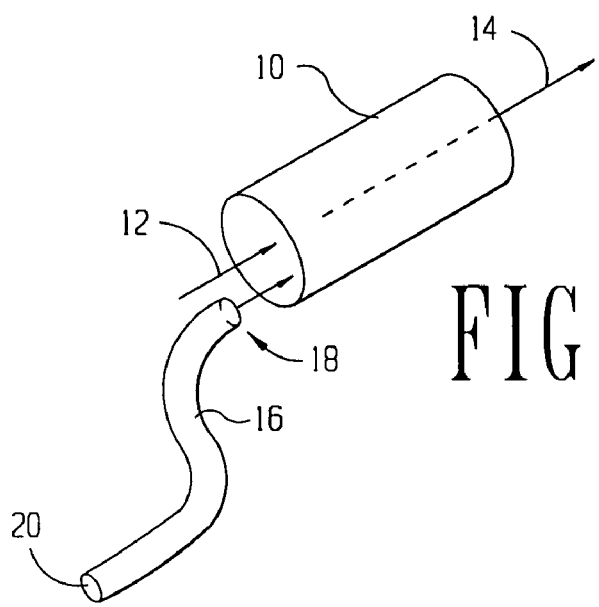
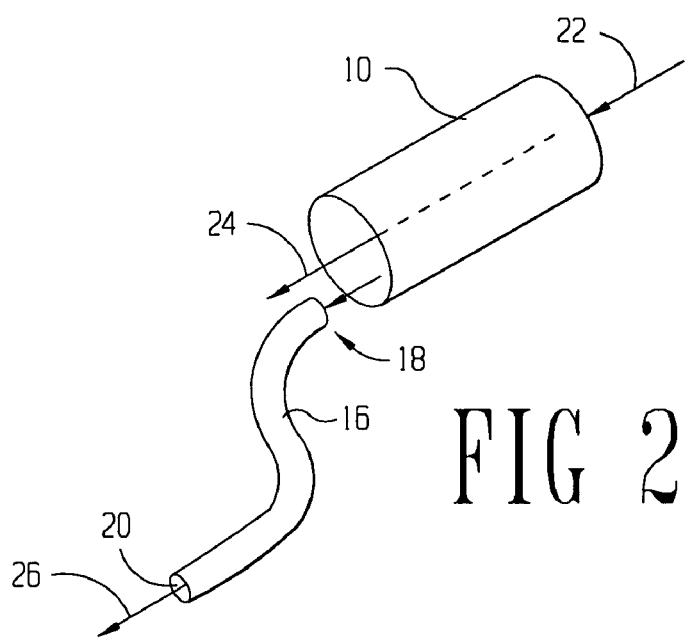
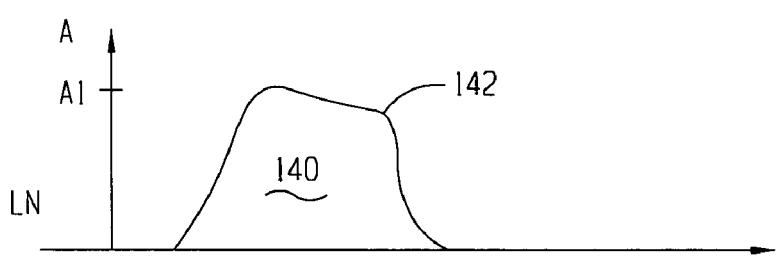
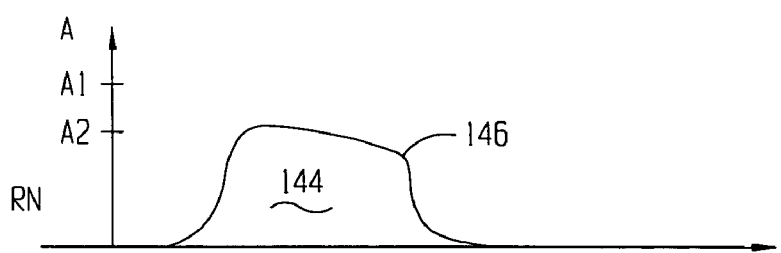
FIG 5

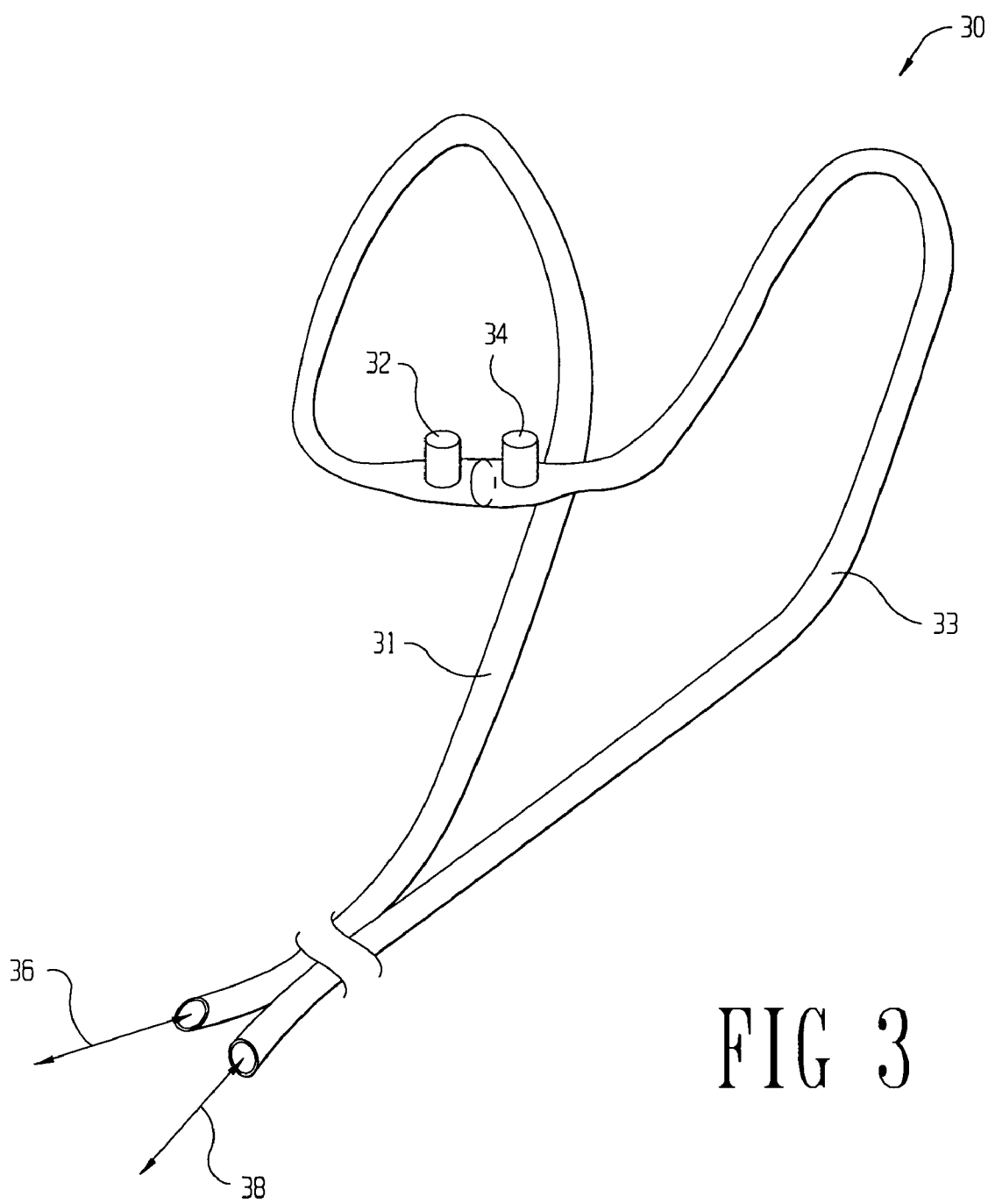

METHOD AND SYSTEM FOR MEASURING AIRFLOW OF NARES

CROSS-REFERENCE TO RELATED APPLICATIONS

None.

STATEMENT REGARDING FEDERALLY SPONSORED RESEARCH OR DEVELOPMENT

Not applicable.

BACKGROUND OF THE INVENTION

1. Field of the Invention

Embodiments of the present invention are directed to measuring relative narial airflow. More particularly, embodiments of the invention are directed to measuring at least a portion of the airflow through nostrils or nares for purposes such as determining differences in flow, and possibly quantifying the airflow.

2. Background of the Invention

Knowing the relative airflow between the nostrils or nares of a person's nose may be useful in predicting or diagnosing many ailments associated with the nose and nasopharynx. For example, relative airflow between the nares may be useful in quantifying a degree of congestion experienced by a patient. Relative airflow may also be useful in determining the degree or extent of a physical abnormality, such as a deviated septum. Moreover, a lack of airflow, or a restriction of airflow, may be a trigger for sleep apnea.

The related art in determining narial airflow may be known as rhinomanography. Rhinomanography may be technique of simultaneously recording nasal pressure by way of a first nostril, and flow through the second, unblocked nostril. By measuring nasal pressure and flow, rhinomanography may allow for the study of the relationships between pressure within the nasal cavities and airflow. Rhinomanography in accordance with the related art may be a multi-step process. In particular, a first naris of a patient may be blocked to prevent airflow, and a pressure gauge or meter may be attached to the blocked naris. Thereafter, the entire nose and mouth of the patient may be covered such that airflow through the unplugged naris may be measured in relation to the pressure developed in the blocked naris. After determining a relationship between the nasal pressure and airflow (through the unblocked naris), the blocked and unblocked naris may be switched and a second set of data may be collected regarding airflow through the second naris with respect to nasal pressure.

As can be appreciated from the description above, a rhinomanographic test may be a complicated process. Airflow measured through each naris is with the other naris plugged, and therefore the relative flow in normal breathing patterns is not determined. By plugging one naris the remaining naris may carry unusually high airflow, which may not be indicative of normal use. Further still, the act of plugging one naris, so as to read nasal pressure, may cause swelling of the nasal tissues, which may in turn affect airflow through that naris, skewing the results.

Thus, what is needed in the art is a method and related system to measure, and possibly quantify, the relative airflow as between nares.

BRIEF SUMMARY OF SOME OF THE EMBODIMENTS

The problems noted above are solved in large part by a method and system for measuring airflow through nares. One exemplary embodiment comprises: measuring an attribute of an airflow through a first naris; measuring an attribute of an airflow through a second naris; wherein measuring the attribute of the airflow through the first naris is accomplished without blocking the second naris; and wherein measuring the attribute of the airflow through the second naris is accomplished without blocking the first naris.

Another exemplary embodiment comprises: a first airflow sensor adapted to detect at least a portion of an airflow through a first naris to create a first measured flow signal; a second airflow sensor adapted to detect at least a portion of an airflow through a second naris to create a second measured flow signal; and a processor electrically coupled to the first and second airflow sensors, wherein the processor is programmed to substantially simultaneously read the first and second measured flow signals.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which:

FIG. 1 illustrates a generic system for sensing attributes of airflow;

FIG. 2 illustrates a generic system for sensing attributes of airflow;

FIG. 3 illustrates a nasal cannula in accordance with embodiments of the inventions;

FIG. 5 illustrates plots of a measured attribute as a function of time in accordance with embodiments of the invention;

NOTATION AND NOMENCLATURE

Figure 4:
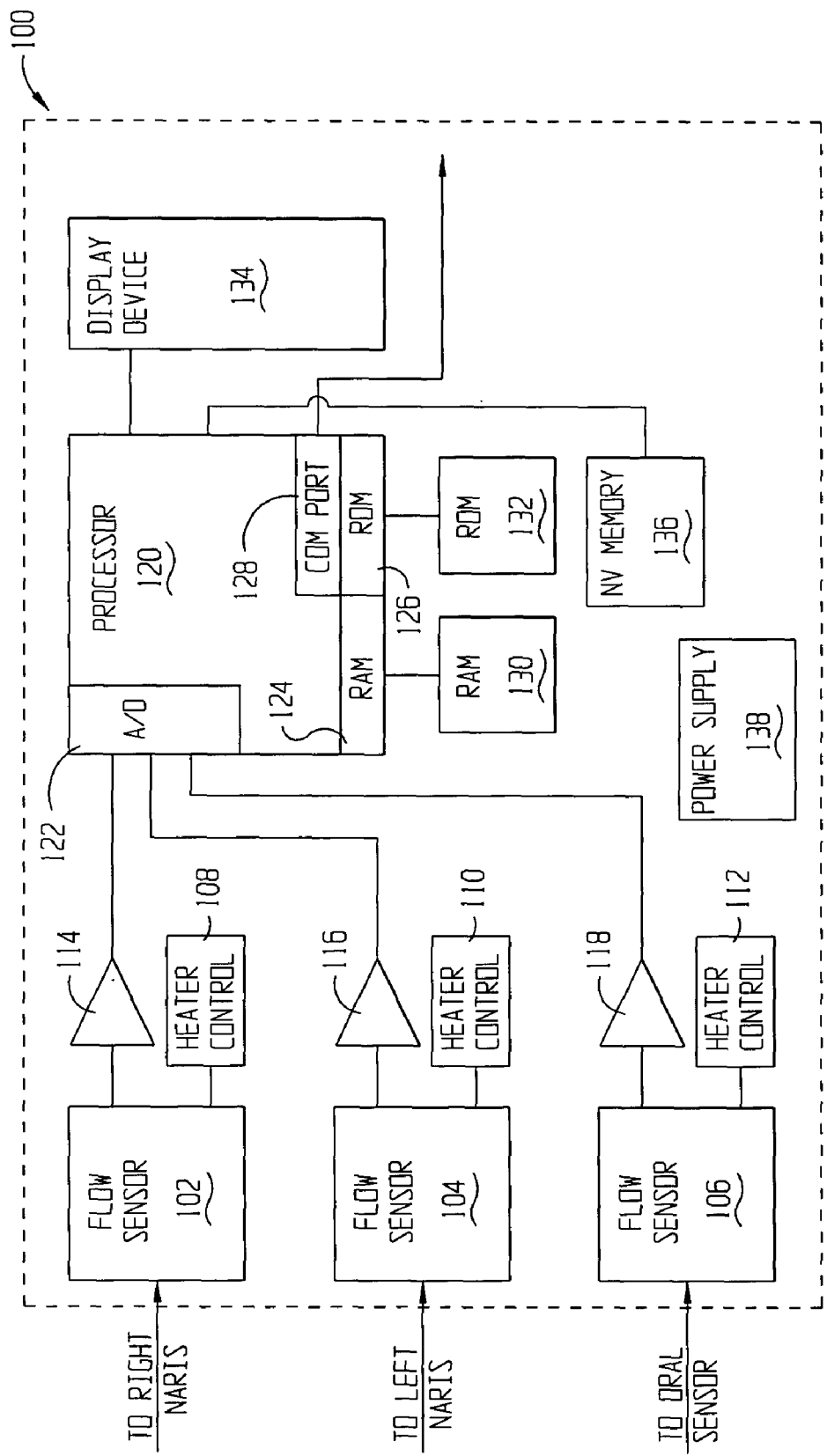
FIG. 4 illustrates a nasal function test device in accordance with embodiments of the invention.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical or mechanical connection. Thus, if a first device couples to a second device, that connection may be through a direct connection, or through an indirect connection via other devices and connections.

DETAILED DESCRIPTION OF THE PREFERRED EMBODIMENTS

The various embodiments of the present invention are directed to determining relative airflow between the nostrils or nares of the nose. The measuring of airflow in each naris may take place substantially simultaneously, and artificial blocking and/or stinting of the nares is preferably avoided, as these acts may cause swelling of the tissue affecting respiration. Knowing the relative airflow between the nares, and possibly quantifying that difference in airflow, may be useful in diagnosing ailments and abnormalities. In the context of describing methods and systems of the various embodiments of the invention, some of the ailments and abnormalities that may be diagnosed using the techniques may be discussed; however, the discussion is not intended to be exhaustive. The methods and systems described herein may be helpful in diagnosing many ailments and abnormalities beyond those specifically mentioned.

Consider for purposes of explanation a generic system as illustrated in FIG. 1. FIG. 1 shows a first pipe or tube 10 having airflow therethrough moving from left to right, as illustrated by arrows 12 and 14. FIG. 1 also illustrates a smaller, possibly flexible, pipe or sensing tube 16 having an end 18 disposed within the airflow entering the tube 10. The sensing tube 16 may also have an end 20, fluidly coupled to the end 18, disposed at some location out or away from the airflow entering the tube 10. Bernoulli's principle states that where the velocity of a fluid, such as air, is high the pressure will be low, and where the velocity of the fluid is low, the pressure will be high. In the generic system illustrated in FIG. 1, the end 18 is defined to be within the airflow entering the tube 10, and thus the air pressure existing proximate to the end 18 of the sensing tube 16 may be lower than the pressure proximate to the end 20. Assuming that end 20 is not blocked to airflow, the difference in pressure may cause an airflow through the sensing tube 16, which airflow continues through the tube 10. Thus, an airflow may be induced in the sensing tube simply by virtue of having one end of the sensing tube placed within the airflow into the larger tube.

Consider now the generic system illustrated in FIG. 2, still comprising the tube 10 and the sensing tube 16, but with the airflow reversed. In particular, airflow may enter the right side of the tube 10 (as illustrated by arrow 22), and exit the left side of the tube 10 (as illustrated by arrow 24). A portion of the air exiting the tube 10 may be hydraulically forced into the end 18 of the sensing tube 16. Because air is hydraulically forced into the sensing tube 16, likewise air may exit the second end 20 of the sensing tube 16 (as indicated by arrow 26). Thus, by virtue of having one end 18 of the sensing tube 16 placed proximate to the tube 10, airflow through the sensing tube 16 may be induced. The amount of airflow induced in the sensing tube 16 in each of the generic situations illustrated in FIGS. 1 and 2 may be proportional to the volume of the airflow through the tube 10.

The principles discussed with respect to FIGS. 1 and 2, in accordance with embodiments of the invention, may be used to determine the relative airflow of the nares of a patient. In particular, sensing tubes may be placed proximate to each naris. As the patient inhales, airflow into the nares may create low pressure areas at the ends of tubes placed proximate to those nares. As discussed with respect to FIG. 1, the low pressure may thus create a differential pressure across the length of the tube, inducing an airflow. During exhalation, exiting gases may be hydraulically forced into the sensing tube, thus inducing flow in a direction opposite that experienced during inhalation.

In alternative embodiments, the tubes may be plugged at their second ends, and the difference, if any, in pressure within the tubes caused by airflow into each naris may be measured. In these alternative embodiments, the pressure induced in the tubes during exhalation may likewise be indicative of the airflow through each nostril.

Although there may be many mechanisms for placing the sensing tubes proximate to the openings in each naris, in the preferred embodiments placement may be accomplished using a nasal cannula. FIG. 3 illustrates a nasal cannula 30 which may be used in accordance with at least some of the embodiments of the invention. As one of ordinary skill in the art is aware, a nasal cannula is positioned on a patient by positioning the apertures 32, 34 proximate to each nostril, running sensing tube 31 over one ear, and running sensing tube 33 over a second ear. The cannula 30 is preferably bifurcated, meaning that sensing tube 31 and aperture 32 may not be fluidly coupled to sensing tube 33 and aperture 34. Thus, airflow through the sensing tube 31, illustrated by arrow 36, may flow only through the aperture 32. Likewise, airflow through sensing tube 33, illustrated by arrow 38 may flow only through the aperture 34. As will be discussed more fully below in relation to an exemplary set of hardware to perform the measuring steps, having each of the apertures 32, 34 allow for determining differences in airflow (or pressure) in each naris. Before proceeding, it should be understood that using a bifurcated nasal cannula such as that illustrated in FIG. 3 is not required to practice and obtain the benefits of the invention. Any mechanism by which the sensing tubes are placed and/or held proximate to the nares falls within the contemplation of the invention.

FIG. 4 illustrates a nasal function test device 100 constructed in accordance with at least some embodiments of the invention. The nasal function test device 100 may comprise a flow sensor 102 adapted to be fluidly coupled to a sensing tube, possibly in operational relationship to a right naris. The sensing tube for the right naris may be, in some embodiments, a portion of the bifurcated nasal cannula as illustrated in FIG. 3. The nasal function test device 100 may also comprise a second flow sensor 104 adapted to be fluidly coupled to a sensing tube, possibly in operational in relationship to a left naris. Likewise, the sensing tube for the left naris may be a portion of a bifurcated nasal cannula as illustrated in FIG. 3. The nasal function test device 100 may also optionally comprise a third flow sensor 106, which may couple to a sensing tube proximate to the mouth of the patient. In accordance with at least some embodiments of the invention, the flow sensors 102, 104 and 106 may be mass flow sensors available from Microswitch (a division of Honeywell Corp.) having part No. AWM92100V. However, other flow sensors may be equivalently used. The preferred flow sensors may operate on the principle of a heated element within the air stream in the flow sensor that experiences different cooling effects depending on airflow. In embodiments using flow sensors such as these, each of the flow sensors 102, 104 and 106 may have a heater control circuit 108, 110 and 112 respectively. Airflow sensors of differing technology may not require the heater control circuits.

The nasal function test device 100 of FIG. 4 may also comprise amplifiers 114, 116 and 118 coupled to an output signal of each of the flow sensors 102, 104 and 106 respectively. The purpose of the amplifiers 114, 116 and 118 may be to amplify the output signals propagating from each of the flow sensors. Depending on the type of flow sensor used, the amplifiers 114, 116 and 118 may not be needed. In accordance with embodiments of the invention, each flow sensor 102, 104 and 106 may produce an output signal that has an attribute that changes proportional to the amount of airflow through the flow sensor. Any attribute of an electrical signal may be used, such as frequency, phase, current flow, or possibly a message based system where information may be coded in message packets. In the preferred embodiments each flow sensor (and related amplifier if used) produces an output signal whose voltage is proportional to the airflow through the sensor. In order that the output signals of the flow sensors may be read and analyzed, each of the flow sensors may couple to a processor 120, possibly through an analog-to-digital (A/D) converter 122.

In the illustration of FIG. 4, processor 120 is shown to have an on-board A/D converter 122, on-board random access memory (RAM) 124, on-board read-only memory (ROM) 126, as well as on-board serial communication ability, as illustrated by communication port 128. In embodiments where these devices (and possibly others) are integral with the processor, the processor may be any of a number of commercially available microcontrollers. Thus, the processor 120 could be a microcontroller produced by Cypress Micro Systems having a part No. CY8C26643. Random access memory, such as RAM 124, may provide a working area for the processor to temporarily store data, and from which programs may be executed. Read-only memory, such as ROM 126, may store programs, such as an operating system, to be executed on the processor 120. ROM may also store user-supplied programs which perform specific tasks. Although microcontrollers may have on-board RAM and ROM, in some embodiments of the invention additional RAM 130 and/or additional ROM 132 may be coupled to the processor 120. In accordance with embodiments of the invention, ROM 126 may store programs specifically designed to perform functions such as a nasal function test. In particular, when executed, the programs may periodically read the signal levels from-the flow sensors 102, 104 and 106. Preferably, the measuring or reading of the signals representing airflow (or other attribute associated with the flow) take place substantially simultaneously. "Substantially simultaneously" shall mean that the signals produced by the flow sensors, or other sensors used, may be read within the same period of time. This, as opposed to, for example, reading the response of a first naris during a first respiratory cycle, the reading the response of a second naris during a different respiratory cycle. Thus, while a single microcontroller or single processor nasal function test device may only be able to read samples one at a time, substantially simultaneously may mean that output signals of multiple measurement sensors may be sample multiple times during a single respiratory cycle.

In alternative embodiments of the invention, the functionality of the microcontroller may be implemented using individual components, such as an individual microprocessor, individual RAM, individual ROM, and an individual A/D converter.

Still referring to FIG. 4, the nasal function test device 100 may further comprise a indicator or display device coupled to the processor 120. While the display device may take many forms, in accordance with embodiments of the invention the display device 134 may comprise a liquid crystal display (LCD), such as an LCD display Part No. TM320240DFG1 available from TIAN-MA Microelectronics Company. Depending on the type of display device 134 used, the processor 120 may communicate information to the user of the nasal function test device 100. In some embodiments, the communication may be by placing alphanumeric characters on the display device 134. In alternative embodiments, the display device 134 may be capable of graphically imparting information to the user of the nasal function test device 100, such as by displaying a graph of the measured flows of the right and left naris (and also possibly the oral flow) as a function of time. In yet further alternative embodiments, the display device 134 may display the information graphically in a portion of a window of the display device 134, and also provide the same or other information in a alphanumeric window. Further still, multiple types of display devices may be used.

The nasal function test device 100 as illustrated in FIG. 4 may also comprise a non-volatile memory 136 coupled to the processor 120. As will be discussed more fully below, in accordance with at least some embodiments of the invention the nasal function test device 100 may have the capability of comparing tests performed on a patient at different times. In order to compare airflows, for example before application of a decongestant and after application of a decongestant, the nasal function test device 100 may need the capability to store the information for later comparison. The non-volatile memory 136 could be battery-backed random access memory, some form of electrically erasable, programmable read-only memory (EPROM), or some other now-existing or after-developed technology. In alternative embodiments, the non-volatile memory 136 may comprise a removable or non-removable disk drive.

The nasal function test device 100 may also comprise a power supply 138. In accordance with at least some embodiments of the invention, the power supply 138 may be capable of taking alternating current (AC) power available at a standard wall outlet and converting it to one or more direct current (DC) voltages for use by the various electronics within the system. In alternative embodiments where the nasal function test device 100 may be portable, the power supply 138 may have the capability of switching between converting the AC wall power to DC, or drawing current from on-board or external batteries, and converting to voltages needed by the devices within the nasal function test device. In yet further embodiments, the power supply 138 may be housed external to the nasal function test device 100.

Having now described the exemplary embodiments of measuring an attribute of the airflow through the nares, the focus of the specification now turns to steps of performing a nasal function test device in accordance with embodiments of the invention. Consider, for purposes of explanation, that a patient has been fitted with a bifurcated nasal cannula such as that illustrated in FIG. 3. Further consider that the sensing tube having an aperture proximate to the right naris is fluidly coupled to the flow sensor 102 of the nasal function test device of FIG. 4, and that the sensing tube having an aperture proximate to the left naris is fluidly coupled to the flow sensor 104. A first test may comprise measuring relative airflow between the left nare and the right nare with the head upright, and during tidal (normal) breathing. A flow sensing system, such as those illustrated in FIG. 4 using a nasal cannula as illustrated in FIG. 3, may only measure a portion of the air which actually enters the naris; however, the amount of airflow through the sensing tube is proportional to the amount of airflow through the naris. A relative airflow between the nares in accordance with embodiments of the invention may be relative in the sense that the airflow through the sensing tube is related to the airflow through the nares, and also relative as between the left naris and the right naris, or both. Determining the relative airflow between the nares with the head upright may be used to quantify con- gestion (particularly if a non-congested airflow is stored in the memory, or possibly a second test may be performed after application of a decongestant), or diagnosing the extent of physical abnormality such as a deviated septum.

A second test that may be performed may be determining relative airflow between the nares with the head upright and taking a deep breath, which may be known as a maximum inspiration. This test may be useful in diagnosing ailments such as nasal valve collapse, or other occlusions of the nares caused by increased airflow.

The inventors of the present specification also envision that a nasal function test device, such as that illustrated in FIG. 4, may be used to determine the relative airflow between the nares with a patient's head tilted to the left or the right (possibly with the patient laying on a side). Determining the relative airflow between the nares in this situation (for both tidal and maximum inspiration) may be useful in diagnosing ailments such as a collapsing nasal valve (which may increase airflow restriction, and therefore increase the possibility of sleep apnea when the patient's head is so positioned during sleep), as well as restrictions in one or both nares caused by the gravitational effects on soft tissue.

Relatedly, the nasal function test may be performed by determining the relative airflow between the nares with the head forward or with the head back (for both tidal and maximum inspiration). These tests too may evidence nasal function abnormality that may not be present with the head upright.

Use of any of these diagnostic methods may be on an individual basis, in any combination of the methods, or possibly using all the diagnostic methods for a complete nasal function study.

Alternative embodiments of the invention may also measure a relative oral airflow in addition to, or in place of, measuring the relative airflow between the nares. Adding the oral component to the comparisons may be helpful, for example, in diagnosing things such as therapeutic responses to medicines, pre and post-operative evaluations, evaluating the side effects of drugs, performing nasal challenge tests (such as determining patient response to allergens), among others.

FIG. 5 illustrates a set of waveforms which may be created based on measured relative airflow between an exemplary left nare (LN) and an exemplary right nare (RN) for a patient. Graphs such as those in FIG. 5 may, in some embodiments, be displayed on the display device 134 (FIG. 4). Although the graphs of FIG. 5 are shown in separate plotted areas, they may be equivalently plotted in the same coordinate axis. Several things should be noted regarding FIG. 5. First, FIG. 5 may illustrate a situation where a patient's airflow through the left nare may be greater than the airflow through the right nare. In this particular example, the peak measured attribute of the airflow for the left nare may reach a value A1. For the same inspiration (or possibly different inspirations), the peak measure flow through the right nare may only reach a value of A2, which is illustrated to be less than the value A1. If the patient under test had the same airflows between the left naris and the right naris with the head upright, but experienced an airflow such as that illustrated in FIG. 5 with the head tilted to the left or right, such a change in relative airflow may be indicative of physical differences or abnormalities, such as a collapsing valve.

Still referring to FIG. 5, in accordance with embodiments of the invention a nasal function test device, such as that illustrated in FIG. 4, may perform scoring of relative airflows. In some embodiments, scoring may comprise integrating to determine the area under each of the airflow curves, the score proportional or equal to the calculated area. Thus, a program executed on processor 120 may integrate to obtain or otherwise calculate the area 140 under the curve 142. Likewise, the processor may integrate to determine the area 144 under the curve 146. The scores may be used later as a comparison of the amount of change, for better or for worse, experienced by the patient with regard to nasal respiration. Though not specifically shown in FIG. 5, a same relative scoring may be done for oral measurements in alternative embodiments.

Figure 6A:
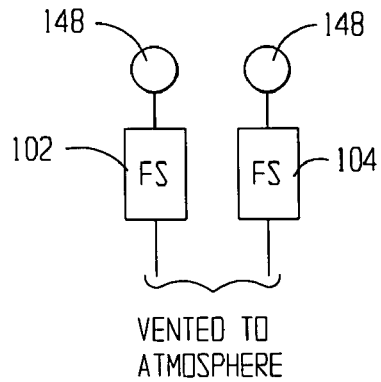
FIG. 6A illustrates, in shorthand form, the nasal function test device of FIG. 4.

In order to discuss various alternative embodiments of the invention, attention is now turned to FIG. 6A which illustrates, in a shorthand notation, a system such as illustrated in FIG. 4. In particular, FIG. 6A shows two nares 148 coupled to flow sensors 102 and 104. Only the flow sensors are illustrated in FIG. 6A; however, some or all of the devices illustrated in FIG. 4 may be assumed to exist in FIGS. 6. In circumstances such as FIG. 6A, one port of each of the flow sensors 102, 104 may be coupled to a sensing tube placed proximate to a naris, and a second port of each of the flow sensors 102, 104 may be vented to the atmosphere. In this way, during inspiration, air may flow in through the vent ports, then through the flow sensors, then through the sensing tubes, and then into the nares. During exhalation, air may flow through the sensing tubes, then through the flow sensors, and then through the vent ports. Flow sensors in accordance with at least embodiments of the invention may be able to provide, in addition to a signal indicating a volume of airflow, an indication of a direction of the airflow through the flow sensor.

Figure 6B:
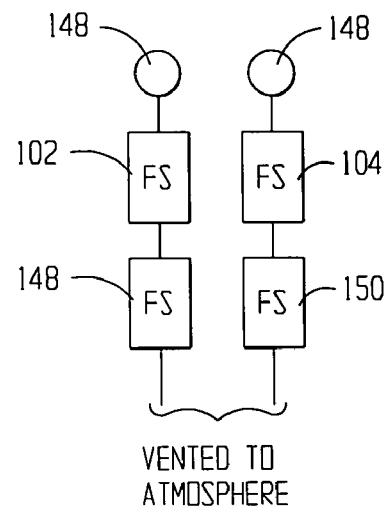
FIG. 6B illustrates alternative embodiments of the nasal function test device of FIG. 4.

Because having a single flow sensor measure both during inspiration and exhalation may limit resolution of the measurements, alternative embodiments of the invention, such as those illustrated in FIG. 6B, may use multiple flow sensors fluidly coupled to each sensing tube. In particular, the embodiments illustrated in FIG. 6B may comprise flow sensors 102 and 104 each coupled to a naris 148, and may also comprise an additional flow sensor 148 coupled to flow sensor 142, and an additional flow sensor 150 coupled to flow sensor 104. For any set of flow sensors coupled together, one flow sensor may be calibrated to obtain measurements in a first direction, and the second flow sensor in the set calibrated to obtain measurements in a second direction. In this way, resolution of the data obtained may be better in each direction than embodiments with only a single flow sensor for each naris.

Figure 6C:
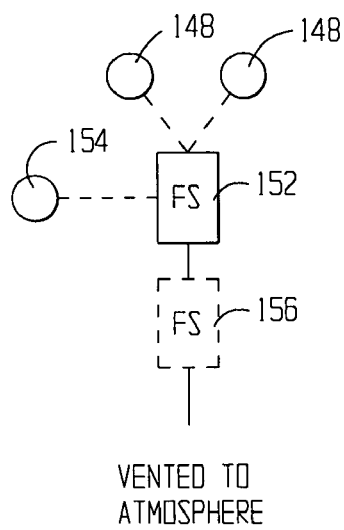
FIG. 6C illustrates alternative embodiments of the nasal function test device of FIG. 4.

In yet further alternative embodiments, the number of flow sensors may be reduced by selectively coupling a single flow sensor to each of the sensing lines. In particular, FIG. 6C illustrates an embodiment having a single flow sensor 152 which may be selectively coupled to either of the nares 148 or to a sensing tube for oral respirations proximate to a mouth 154. Although the preferred embodiments measure airflow in the nares (and possibly through the mouth) substantially simultaneously, in the alternative embodiments the relative airflow measurement of each naris (and possibly the mouth) may take place individually. Much like the differences between the exemplary embodiments in FIGS. 6A and 6B, the embodiments of FIG. 6C may also comprise an additional flow sensor 156 coupled in series with the first flow sensor 152 for obtaining improved resolution during both inhalation and exhalation.

Figure 6D:
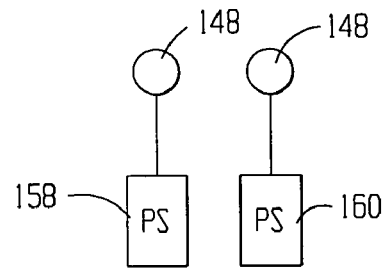
FIG. 6D illustrates alternative embodiments of the nasal function test device of FIG. 4.

As was alluded to in the section describing the physics associated with sensing airflow, when a sensing tube is blocked to airflow through the tube, yet having an aperture within the airflow of a naris, pressures may be developed inside the sensing tube proportional to the airflow through the naris. Thus, during inspiration the airflow by the end of the sensing tube may create a low pressure, which low pressure may be sensed by measuring pressure within the sensing tube. Likewise, during exhalation air may be hydraulically forced into the sensing tube, causing increased pressure, which may likewise be sensed. FIG. 6D illustrates alternative embodiments of the invention that may sense pressure in blocked sensing tubes as an alternative to sensing flow through those tubes. FIG. 6D illustrates, in the same shorthand notations as FIG. 6A-C, a system where a pressure sensor 158 couples by way of a sensing tube to one of the naris 148, and a second pressure sensor 160 couples to the remaining of the nares 148 by a sensing tube. In this embodiment, as a patient inhales, pressure sensors 158 and 160 may create signals proportional to a drop in pressure within the sensing tubes (which drop in pressure is proportional to the amount of airflow through the nares). Likewise, during exhalation, the pressure sensors 158 and 160 may sense increased pressures within the sensing tube caused by the air exiting the nares being hydraulically forced into the sensing tubes. Pressure sensors produced by Motorola® having part number MPXV5004DP may be used in these embodiments. In an exemplary pressure case, the difference in pressure sensed between the nares may be indicative of the difference in airflow between those nares.

Figure 6E:
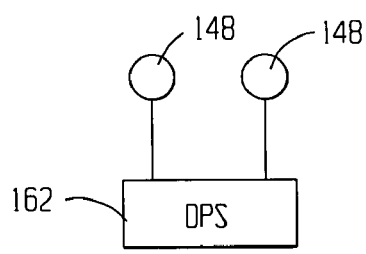
FIG. 6E illustrates alternative embodiments of the nasal function test device of FIG. 4.

Yet other alternative embodiments, illustrated in FIG. 6E, may use a single differential pressure sensor 162 having a first port coupled to a sensing tube in relation to one of the nares 148, and a second port coupled to a sensing tube in relation to a second of the nares 148. The differential pressure sensor 162 may produce an output signal proportional to the difference in sensed pressure (and therefore proportional to the difference in airflow) between the nares 148.

Measuring an attribute of an airflow through the nares to this point has assumed that the sensing tubes have their respective apertures proximate to the entrance or opening of each naris. This, however, is not required. In alternative embodiments, at least one of the apertures of the sensing tubes may be placed a known distance into its respective naris. By selectively increasing the distance into the naris (or alternatively decreasing the distance within the naris), and running a plurality of nasal function tests, it may be possible to determine a distance within a naris at which an abnormality or occlusion may be located.

The above discussion is meant to be illustrative of the principles and various embodiments of the present invention. Numerous variations and modifications will become apparent to those skilled in the art once the above disclosure is fully appreciated. For example, it may be possible to measure a complete airflow through each naris by sealing a measurement device at the opening of the naris. In accordance with at least some embodiments, however, the sealing should not act to stint open the nasal valve. It is intended that the following claims be interpreted to embrace all such variations and modifications:

What is claimed is:

1. A method comprising:
    measuring at least a portion of an airflow of a first naris through a first sensing tube, the measuring creates a first measured airflow; and
    measuring at least a portion of an airflow of a second naris through a second sensing tube fluidly independent of the first sensing tube, the measuring creates a second measured airflow;
    wherein measuring at least a portion of the airflow of the first naris is accomplished without blocking the second naris; and
    wherein measuring at least a portion of the airflow of the second naris is accomplished without blocking the first naris.

2. The method as defined in claim 1 wherein the measuring take place during inhalation.

3. The method as defined in claim 1 wherein the measuring takes place during exhalation.

4. The method as defined in claim 1 wherein measuring at least a portion of the airflow of the first naris further comprises measuring at a known distance within the first naris.

5. The method as defined in claim 1 wherein measuring at least a portion of the airflow of the first naris further comprises measuring the airflow through the first sensing being part of tube of a bifurcated nasal cannula worn by a patient.

6. The method as defined in claim 1 further comprising determining a difference in the first and second measured airflows.

7. The method as defined in claim 1 wherein the measuring takes place substantially simultaneously.

8. The method as defined in claim 1 further comprising measuring at least a portion of an oral airflow.

9. The method as defined in claim 8 wherein the measuring further comprises measuring substantially simultaneously.

10. A method comprising:
    measuring a pressure associated with an airflow through a first naris, the measuring by way of a first sensing tube; and
    measuring a pressure associated with an airflow through a second naris, the measuring the pressure associated with airflow through the second naris by way of a second sensing tube, the first and second sensing tubes fluidly independent;
    wherein measuring the pressure associated with the airflow through the first naris is accomplished without blocking the second naris; and
    wherein measuring the pressure associated with the airflow through the second naris is accomplished without blocking the first naris.

11. The method as defined in claim 10 wherein the measuring further comprises measuring a pressure proximate to an opening of each of the first and second naris.

12. The method as defined in claim 10 further comprising determining a difference in the pressure measured between the first and second naris.

13. The method as defined in claim 10 wherein the measuring takes place during inhalation.

14. The method as defined in claim 10 wherein measuring the pressure associated with the airflow through the first naris further comprises measuring a pressure in the first sensing tube being part of a bifurcated nasal cannula.

15. A nasal function test device comprising:
    a first air mass flow sensor configured to fluidly couple to a first naris by way of a first sensing tube, the first air mass flow sensor detects airflow of the first naris that flows through the first sensing tube to create a first measured flow signal;
    a second air mass flow sensor configured to fluidly couple to a second naris by way of a second, fluidly independent sensing tube, the second air mass flow sensor detects airflow of the second naris that flows through the second sensing tube to create a second measured flow signal; and a processor electrically coupled to the first and second airflow sensors, and wherein the processor is programmed to substantially simultaneously read the first and second measured flow signals.

16. The nasal function test device as defined in claim 15 further comprising:

a third air mass flow sensor coupled to the processor, the third air mass flow sensor detects at least a portion an oral airflow to create a measured oral flow signal; and wherein the processor is programmed to substantially simultaneously read the first measured flow signal, the second measured flow signal, and the measured oral flow signal.

17. The nasal function test device as defined in claim 15 wherein the processor is further programmed to determine a difference between the first and second measured flow signals.

18. The nasal function test device as defined in claim 15 further comprising a display device coupled to the processor and wherein the processor displays an indication of the first and second measured flow signals on the display device.

19. The nasal function test device as defined in claim 18 wherein the display device displays a graph of the first and second measured flow signals as a function of time.

20. The nasal function test device as defined in claim 18 wherein the display device displays a difference between the first and second measured flow signals.

21. The nasal function test device as defined in claim 15 further comprising:

a non-volatile memory coupled to the processor; and wherein the processor is programmed to store the first and second measured flow signals as a first set of data in the non-volatile memory, and wherein the processor is further programmed to analyze differences between the first set of data in the non-volatile memory and a second set of data taken at a different time.

22. The nasal function test device as defined in claim 15 further comprising:

a bifurcated nasal cannula comprising the first sensing tube and the second sensing tube.

23. The nasal function test device as defined in claim 22 wherein the first sensing tube has an opening positioned within the airflow of the first naris.

24. The nasal function test device as defined in claim 23 wherein the opening of the first sensing tube is proximate to an entrance to the first naris.

25. The nasal function test device as defined in claim 23 wherein the opening of the first sensing tube is a measurable distance within the first naris.

26. The nasal function test device as defined in claim 15 further comprising third air mass flow sensor fluidly coupled to the first air mass flow sensor, and wherein the first air mass flow sensor produces the measured flow signal during inhalation, and wherein the third air mass flow sensor produces a measured flow signal during exhalation.

27. A nasal function test device comprising:

a first airflow sensor that detects at least a portion of an airflow through a first naris to create a first measured flow signal;

a second airflow sensor that detects at least a portion of an airflow through a second naris to create a second measured flow signal; and a processor electrically coupled to the first and second airflow sensors, and wherein the processor is programmed to substantially simultaneously read the first and second measured flow signals;

wherein the processor is further programmed to determine an area under a curve produced by changes in the first measured flow signal during at least one of inhalation or exhalation, the area being a first breathing score;

wherein the processor is further programmed to determine an area under a curve produced by changes in the second measured flow signal during at least one of inhalation or exhalation, the area being a second breathing score; and wherein the processor determines a difference between the first and second breathing score.

28. A system comprising:

a differential pressure measurement device having first and second ports, wherein the first port is configured to be fluidly coupled to a first nostril of a patient, and wherein the second port is configured to be fluidly coupled to a second nostril of a patient;

an indicator coupled to the differential pressure measurement device, and wherein the indicator displays an indication of a difference in air pressure associated with airflow in each of the first and second nostrils.

29. The system as defined in claim 28 wherein the indicator further comprises a display device that provides a plot of the pressure reading taken by the differential pressure device as a function of time.

30. A system comprising:

a differential pressure measurement device having first and second ports, wherein the first port is configured to be fluidly coupled to a first nostril of a patient, and wherein the second port is configured to be fluidly coupled to a second nostril of a patient;

an indicator coupled to the differential pressure measurement device, and wherein the indicator displays an indication of a difference in air pressure associated with airflow in each of the first and second nostrils;

a nasal cannula having a first and second sensing lines, the first and second sensing lines not in fluid communication; and wherein the first sensing line couples to the first port, and wherein the second sensing line couples to the second port.

31. A method comprising:

measuring a relative airflow as between the nostrils of a patient with the patient's head held in a first position and at a first respiratory rate;

measuring a relative airflow as between the nostrils of the patient with the patient's head held in a second position and at a second respiratory rate;

wherein the first and second position are one each selected from the group of: head upright, head tilted left, head tilted left, head facing down or head facing up; and wherein the first and second respiratory rate are one each selected from the group of: tidal breathing or maximum inspiration.

32. The method as defined in claim 31 further comprising determining whether there are differences in measured relative airflow between the first position and the second position.

33. The method as defined in claim 31 wherein measuring the relative airflow as between the nostrils of a patient with the patient's head held in a first position further comprises measuring without blocking either nostril.

34. The method as defined in claim 33 wherein measuring the relative airflow as between the nostrils of the patient with the patient's head held in a second position further comprises measuring without blocking either nostril.

35. The method as define in claim 31 further comprising:
   measuring oral airflow with the patient's head in the first position; and
   measuring oral airflow with the patient's head in the second position.

36. A nasal function test device comprising:
   a first pressure sensor configured to fluidly couple to a first naris by way of a first sensing tube, the first pressure sensor detects a pressure associated with an airflow through the first naris to create a first measured signal;
   a second pressure sensor configured to fluidly couple to a second naris by way of a second sensing tube, the second sensing tube fluidly independent of the first sensing tube, and the second pressure sensor detects a pressure associated with an airflow through the second naris to create a second measured signal; and
   a processor electrically coupled to the first and second pressure sensors, and wherein the processor is programmed to substantially simultaneously read the first and second measured signals.

37. The nasal function test device as defined in claim 36 wherein the processor is further programmed to determine a difference between the first and second measured signals.

38. The nasal function test device as defined in claim 36 further comprising a display device coupled to the processor, and wherein the processor displays an indication of the first and second measured signals on the display device.

39. The nasal function test device as defined in claim 38 wherein the display device displays a graph of the first and second measured signals as a function of time.

40. The nasal function test device as defined in claim 38 wherein the display device displays a difference between the first and second measured signals.

41. The nasal function test device as defined in claim 36 further comprising:
   a non-volatile memory coupled to the processor; and
   wherein the processor is programmed to store the first and second measured signals as a first set of data in the non-volatile memory, and wherein the processor is further programmed to analyze differences between the first set of data in the non-volatile memory and a second set of data taken at a different time.

42. The nasal function test device as defined in claim 36 further comprising:
   a bifurcated nasal cannula comprising the first sensing tube and the second sensing tube.

43. A method comprising:
   measuring at least a portion of an airflow of a first naris through a first sensing tube, the measuring creates a first measured airflow; and substantially simultaneously
   measuring at least a portion of an airflow of a second naris through a second, fluidly independent sensing tube, the measuring creates a second measured airflow.

44. The method as defined in claim 43 where measuring further comprises measuring at least a portion of the airflow with a respective mass flow sensor.

45. The method as defined in claim 43 wherein the measuring takes place during inhalation.

46. The method as defined in 44 wherein measuring further comprises measuring at least a portion of the airflow with the respective mass flow sensor fluidly coupled to the respective naris by a sensing tube of a bifurcated nasal cannula.

* * * * *